United States Patent
Mewissen et al.

(10) Patent No.: US 7,326,944 B2
(45) Date of Patent: Feb. 5, 2008

(54) COLLAPSIBLE IRRADIATION DEVICE

(75) Inventors: Jan Alfons Catharina Mewissen, Drachten (NL); Harko Jan Taekema, Drachten (NL); Olaf Martin De Jong, Drachten (NL); Rogier Hille, Groningen (NL)

(73) Assignee: Koninklijke Philips Electronics N.V., Eindhoven (NL)

( * ) Notice: Subject to any disclaimer, the term of this patent is extended or adjusted under 35 U.S.C. 154(b) by 84 days.

(21) Appl. No.: 10/554,228

(22) PCT Filed: Apr. 26, 2004

(86) PCT No.: PCT/IB2004/050510

§ 371 (c)(1), (2), (4) Date: Oct. 25, 2005

(87) PCT Pub. No.: WO2004/096363

PCT Pub. Date: Nov. 4, 2004

(65) Prior Publication Data
US 2007/0023687 A1 Feb. 1, 2007

(30) Foreign Application Priority Data
Apr. 28, 2003 (EP) .................................. 03101162

(51) Int. Cl.
*G01J 1/00* (2006.01)

(52) U.S. Cl. .............................. 250/504 R; 250/491.1; 368/10

(58) Field of Classification Search ............. 250/504 R
See application file for complete search history.

(56) References Cited

U.S. PATENT DOCUMENTS 4,074,164 A * 2/1978 Leyendecker ................ 313/25
5,084,810 A * 1/1992 Huang ........................ 362/410
5,339,233 A * 8/1994 Yang ......................... 362/402

* cited by examiner

*Primary Examiner*—David Vanore
*Assistant Examiner*—Phillip A Johnston
(74) *Attorney, Agent, or Firm*—Paul Im

(57) ABSTRACT

An irradiation device includes a base part, a support longitudinally extending from the base part and enclosing an angle with a vertical axis, and a housing that includes a central axis, at least one radiation unit, and a radiation emission plane. The housing is pivotally connected to the support via a pivot shaft and is pivotable between an operational position in which the radiation emission plane is horizontal, and a rest position in which the radiation emission plane vertical with a single rotation of the pivot shaft about a pivot axis extending through the pivot shaft.

11 Claims, 4 Drawing Sheets

Figure 1:
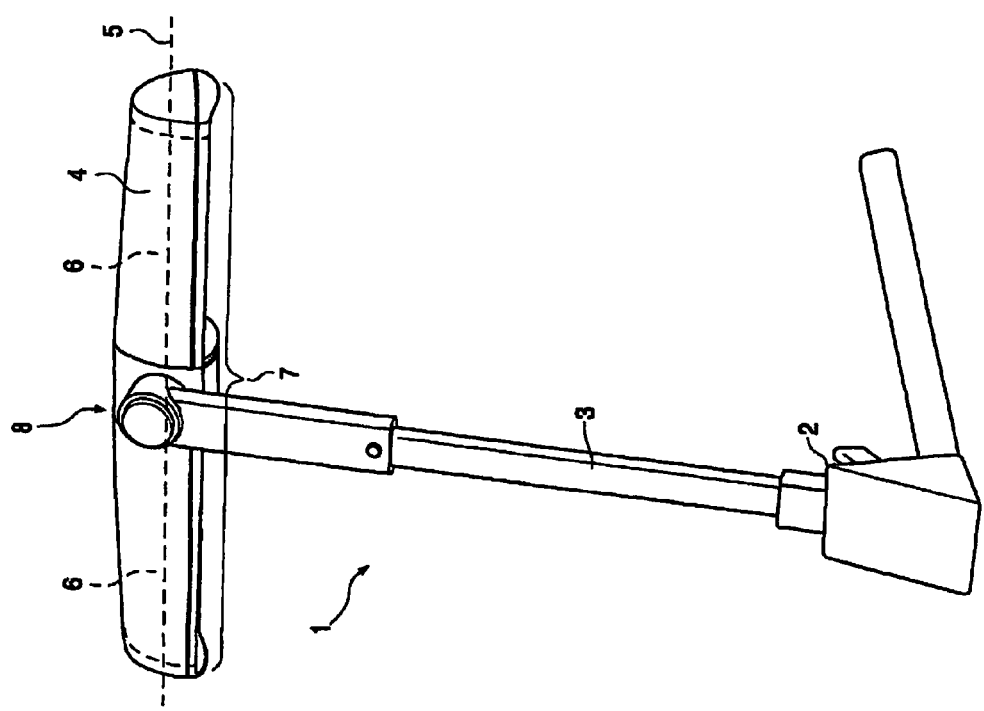

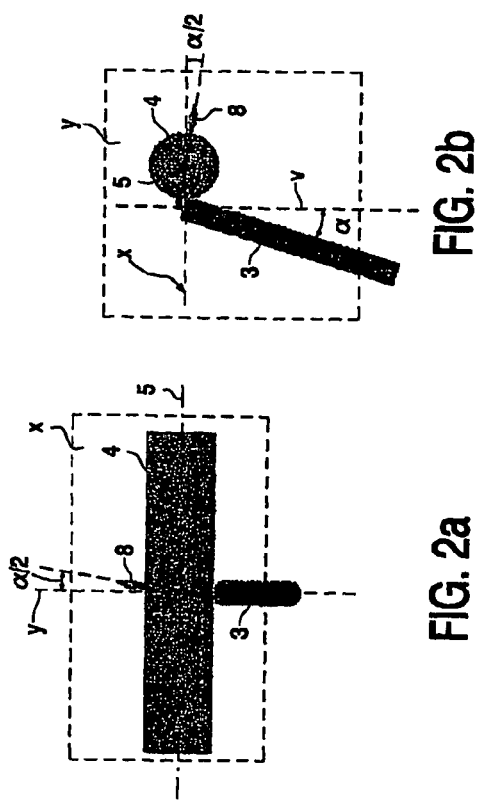
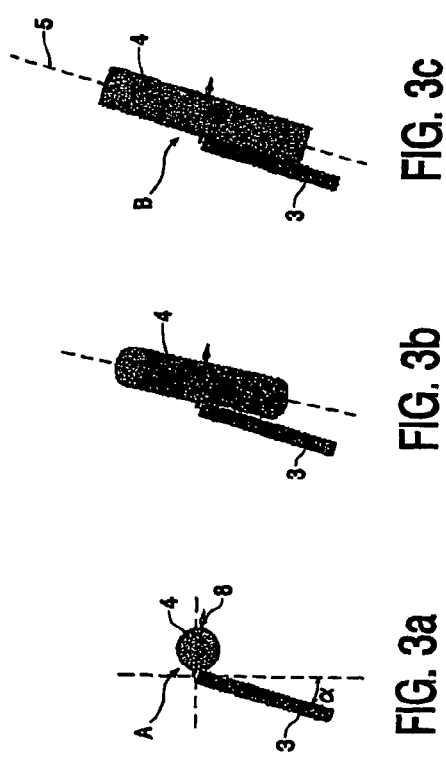

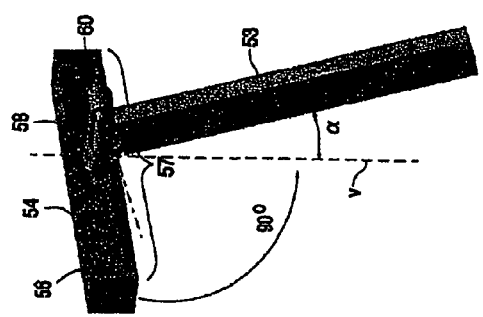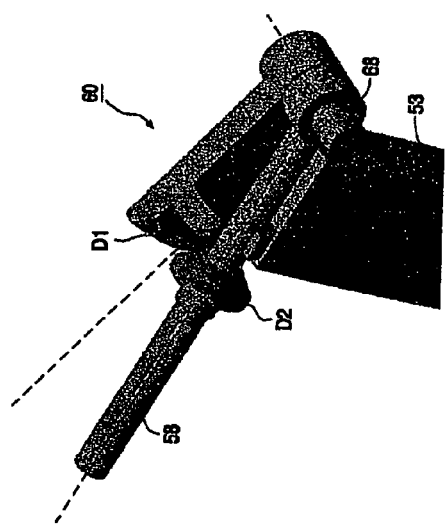

COLLAPSIBLE IRRADIATION DEVICE

The invention relates to an irradiation device comprising a base part, a support longitudinally extending from the base part and enclosing an angle (α) with a vertical axis, and a housing comprising a central axis, at least one radiation unit, and a radiation emission plane, said housing being pivotally connected to said support via a pivot shaft so as to be pivotable between an operational position, in which the radiation emission plane is horizontal, and a rest position, in which the radiation emission plane is vertical, and the central axis of the housing encloses the angle (α) with the vertical axis.

An irradiation device of the type described in the opening paragraph is generally known. A known irradiation device is used, for example, for irradiating the human body with ultraviolet radiation. The support extends longitudinally from the base part, enclosing an angle with a vertical axis. The housing is provided with an ultraviolet radiation unit, and in operation the ultraviolet radiation leaves the housing through the radiation emission plane. Said housing is pivotally connected to the support via a pivot shaft. In the operational position of the housing the radiation emission plane is horizontal, and in the rest position the radiation emission plane is vertical, the central axis of the housing enclosing the angle (α) with the vertical axis. After use the device can be folded into a more compact configuration for storage purposes in that the housing is rotated about the pivot shaft relative to the support.

A user has to execute two rotational operations to move the housing into a position parallel with the support. First, the housing has to be rotated from its operational position into a position in which the radiation emission plane is vertical. Then the housing has to be rotated within this vertical plane towards the rest position in which the central axis of the housing encloses the angle (α) with the vertical axis. This is cumbersome for the user, and it requires additional hinge points which render the construction more expensive and vulnerable.

It is an object of the invention to provide an irradiation device which is easily collapsible and which has a solid folding mechanism. To achieve this object, an irradiation device according to the invention is characterized in that the pivot shaft extends from the support so as to enclose an angle (α/2) with the horizontal plane and with the vertical plane. Because of the arrangement of the pivot shaft at this angle relative to both these planes, the housing can be fluently rotated about the pivot shaft between the operational position and the rest position. The movement of the housing from the operational position to the rest position, and vice versa, requires only a single rotation about a single pivot axis. This is advantageous both when the irradiation device is to be put up before use and when it is to be stored after use, and thus enhances the user-friendliness of the device. Furthermore, in this manner no additional hinge points are required, which renders it a solid construction.

An embodiment of an irradiation device according to the invention is characterized in that a blocking system is provided for releasably blocking the housing in its operational position and in its rest position relative to the support. In this manner it is ensured that the housing maintains its intended position relative to the support, which is especially important for the operational position in view of user safety.

An embodiment of an irradiation device according to the invention is characterized in that the blocking system comprises a cylindrical blocking element with protrusions which is provided coaxially with the pivot shaft near an end of the pivot shaft in the vicinity of its connection to the support, and a chamber provided in the housing for receiving said blocking element, comprising notches for co-operation with said protrusions. This provides an advantageous construction of the blocking system.

A further embodiment of an irradiation device according to the invention is characterized in that a connection system is provided for connecting the pivot shaft to the support, which system comprises a fastening element for receiving the shaft, which fastening element is attachable to the support, and a clamp element for clamping the shaft in said fastening element.

An embodiment of an irradiation device according to the invention is characterized in that the device comprises a suntanning device.

Figure 4:
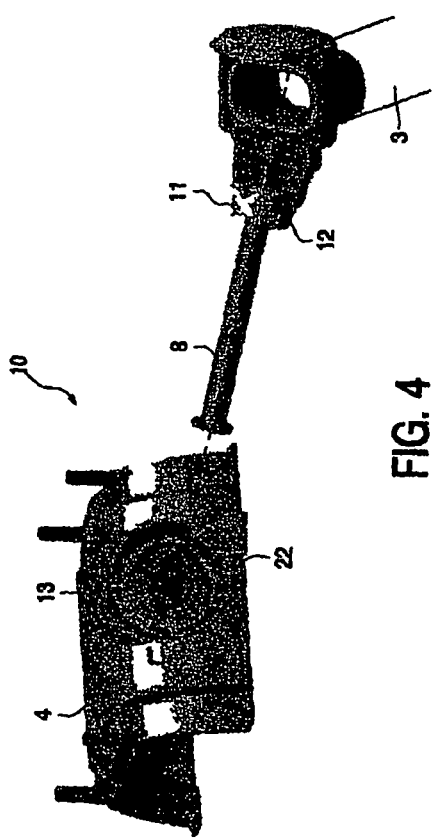
Figure 5:
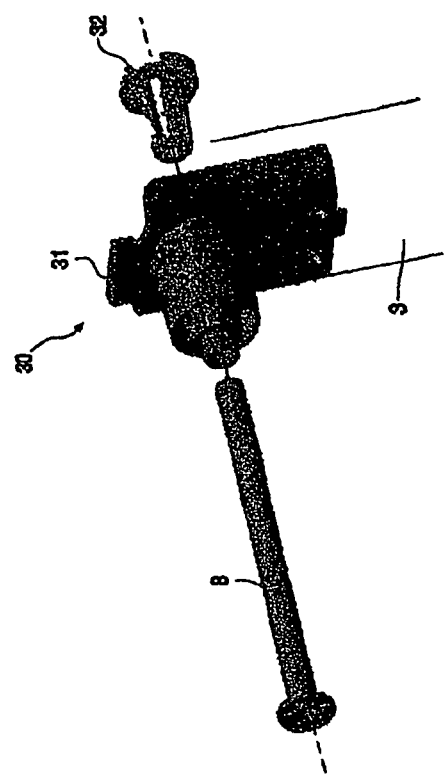

The invention will be described in more detail hereinafter with reference to the drawings, in which FIG. 1 is a perspective view of an embodiment of an irradiation device according to the invention, FIGS. 2a and b are a schematic top view and a schematic side view, respectively, of an upper part of the irradiation device of FIG. 1, FIGS. 3a, b and c are schematic side views of the irradiation device of FIG. 1 when it is being moved from an operational position into a rest position, FIG. 4 is an exploded view of a blocking system of the irradiation device according to the invention, FIG. 5 is an exploded view of a connection system of a further embodiment of an irradiation device according to the invention, and FIGS. 6a and 6b are a schematic view of a further irradiation device and a schematic view of an upper part of the irradiation device of FIG. 6a, respectively.

FIG. 1 shows an irradiation device 1 according to the invention, comprising a base part 2 and a support 3 longitudinally extending from the base part 2 at an angle a relative to a vertical axis V. It is noted that, although this embodiment of the device is a suntanning device, it may alternatively comprise other types of irradiation devices. The device furthermore comprises a housing 4 comprising a central axis 5, at least one radiation unit 6, and a radiation emission plane 7. The radiation unit 6 in this embodiment comprises compact HPA lamps, but it is noted that any known type of radiation source may be applied. The radiation emission plane 7 is the plane through which the radiation leaves the housing during operation of the device. The housing 4 is pivotally connected to said support 3 via a pivot shaft 8. The housing 4 is pivotable between an operational position A (see FIGS. 2a and 3a), in which the radiation emission plane is horizontal (X), and a rest position B, in which the radiation emission plane is vertical (Y), and the central axis 5 of the housing 4 encloses the angle (α) with the vertical axis, in this embodiment extending parallel to the support (see FIG. 3c).

As can be seen in FIGS. 2a and b, the pivot axis 8 extends from the support 3 enclosing an angle (α/2) with the vertical plane Y and with the horizontal plane X. In this manner the housing can be moved from its operational position A shown in FIG. 3a into its rest position B shown in FIG. 3c by means of a single rotation about a single pivot axis. FIG. 3b shows an in-between position of the housing between the positions A and B, which is not a static position, but a position that occurs during the fluent movement of the housing about the pivot shaft 8 from position A to B. Since the pivot shaft is arranged in the above described manner, the device according to the invention can be easily folded for storage purposes, which enhances the user-friendliness of the irradiation device, while it also provides a solid construction.

FIG. 4 is an exploded view of a blocking system 10 of an irradiation device 1 according to the invention. The blocking system 10 is provided for releasably blocking the housing 4 in its operational position A and in its rest position B relative to the support 3. In this embodiment, the blocking system 10 comprises a blocking element 11 with protrusions 12, which is provided coaxially with the pivot shaft 8 near an end of the pivot shaft 8 in the vicinity of its connection to the support 3. A chamber 13 for receiving said blocking element 11 is provided in the housing 4, here shown as an inner part of the housing, said chamber 13 comprising notches 22 for co-operation with said protrusions 12. The notches receive the protrusions in dependence on the rotational movement of the housing, and thus of the chamber, relative to the pivot shaft, and thus relative to the blocking element. This construction ensures that the housing 4 maintains the position in which it is set by the user, this position being either the operational position or the rest position. In the operational position, the blocking system prevents an unsafe situation for the user of the device, which would occur if the housing were to rotate by itself about the pivot shaft while a user is present beneath the radiation emission plane. In the rest position, the blocking system prevents damage to the housing or objects present near the device, which would occur if the housing were to rotate by itself about the pivot shaft while it is stored away.

FIG. 5 is an exploded view of a connection system 30 of a further embodiment of an irradiation device according to the invention. The connection system 30 is provided for connecting the pivot shaft 8 to the support 3 and comprises a fastening element 31 for receiving the shaft 8, which element is attached to the support 3, and a clamp element 32 for clamping the shaft 8 in said fastening element. It is noted that other types of connection systems may alternatively be used to connect the axis to the support. For example, the connection system as shown in FIG. 4 may be applied, this system comprising two housing parts which are connectable to the support and between which the shaft is clamped.

It is noted that, although the irradiation device as described in the above embodiments comprises a suntanning device, the irradiation device according to the invention may also comprise other types of irradiation devices. Medical irradiation devices and devices for illumination, for example, may also benefit from the advantages resulting from the invention.

It is noted that other means may be provided for easily moving the housing between the operational position and the rest position in an irradiation device comprising a base part, a support longitudinally extending from the base part and enclosing an angle ($\alpha$) with a vertical axis, and a housing comprising a central axis, at least one radiation unit, and a radiation emission plane, said housing being pivotally connected to said support via a pivot shaft so as to be pivotable between an operational position, in which the radiation emission plane is horizontal, and a rest position, in which the radiation emission plane is vertical, and the central axis of the housing encloses the angle ($\alpha$) with the vertical axis.

Said means may comprise a gear system comprising a first gear wheel provided at the connection point of the support to the lamp housing, a second gear wheel engaging the first gear wheel, connected to the lamp housing, and rotatable about the pivot shaft, the diameter of the first gear wheel being related to the diameter of the second gear wheel as follows: first gear wheel diameter=second gear wheel diameter$\times(90/\alpha)$. In this manner the housing can be moved by the user from the operational position into a position parallel with the support by means of only one rotational operation. This is advantageous both when the irradiation device is to be put up before use and when it is to be stored after use, and thus enhances the user-friendliness of the device.

FIG. 6a shows an irradiation device according to the invention, comprising a base part (not shown), a support 53 longitudinally extending from the base part and enclosing an angle ($\alpha$) with a vertical axis V, a housing 54 comprising a central axis, at least one radiation unit 56, and a radiation emission plane 57, said housing being pivotally connected to said support via a pivot shaft 58, said housing being pivotable between an operational position, in which the radiation emission plane is horizontal, and a rest position, in which the radiation emission plane is vertical, and the central axis of the housing encloses the angle ($\alpha$) with the vertical axis. It is noted that, although this embodiment of the device is a suntanning device, it may also comprise other types of irradiation devices.

FIG. 6b shows an upper part of the irradiation device in more detail. The gear system 60 comprises a first gear wheel D1 provided at the connection point of the support 53 to the housing 54, and a second gear wheel D2 for co-operation with the first gear wheel D1, which is connected to the housing 54 (not shown in the Figure) and is rotatable about the pivot shaft 58. The second gear wheel D2 is fixedly fastened to the housing and can only rotate together with the housing. The pivot shaft 58 is pivotally connected to the support 53 via a further pivot shaft 68. The diameter of the first gear wheel D1 is related to the diameter of the second gear wheel D2 as follows: first gear wheel diameter D1=second gear wheel diameter D2$\times(90/\alpha)$. With this gear ratio, the housing 54 can be moved in one rotational movement through 90° from the operational position into the rest position parallel to the support, and vice versa. In this embodiment, the gear wheels D1 and D2 comprise conoid gear wheels, but it is noted that other known types of gear wheels may alternatively be applied.

The invention claimed is:

1. An irradiation device comprising:
a base;
a support longitudinally extending from the base; and
a housing comprising at least one radiation unit and a radiation emission plane; and
a shaft which pivotally connects the housing to the support; the housing being pivotable between an operational position where the radiation emission plane is horizontal, and a rest position where the radiation emission plane is vertical;
wherein the housing is movable between the operational position and the rest position with a single rotation of the shaft about a pivot axis extending through the shaft; and a gear system at the connection point of the support to the housing.

2. The irradiation device as claimed in claim 1, wherein the device comprises a sun-tanning device.

3. The irradiation device of claim 1, wherein the support encloses a first angle having a first value with a vertical axis, and wherein a central axis of the housing encloses a second angle having the first value with the vertical axis.

4. The irradiation device of claim 1, wherein the support encloses a first angle having a first value with a vertical axis, and wherein the shaft extends from the support so as to enclose a second angle having a second value with the horizontal plane and with the vertical plane, the second value being half the first value.

5. The irradiation device of claim 1, further comprising:
   a fastening element that receives the shaft and is attachable to the support; and
   a clamp which clamps the shaft in the fastening element.

6. The irradiation device of claim 1, further comprising a first gear having a first diameter D1 and engaging a second gear having a second diameter D2, the second gear being rotatable about the shaft, wherein $D1=D2(90/\alpha)$, where $\alpha$ is an angle between the support and a vertical axis.

7. An irradiation device comprising:
   a base;
   a support extending from the base; and
   a housing comprising at least one radiation unit and having a longitudinal axis; and
   a shaft which pivotally connects the housing to the support; the housing being pivotable between a rest position where the longitudinal axis is substantially parallel to the support and an operational position where the longitudinal axis is not substantially parallel with the support;
   wherein the housing is movable between the operational position and the rest position with a single rotation of the shaft about a pivot axis extending through the shaft: and a gear system at the connection point of the support to the housing.

8. The irradiation device of claim 7, wherein the support encloses a first angle having a first value with a vertical axis, and wherein a central axis of the housing encloses a second angle having the first value with the vertical axis.

9. The irradiation device of claim 7, wherein the support encloses a first angle having a first value with a vertical axis, and wherein the shaft extends from the support so as to enclose a second angle having a second value with the horizontal plane and with the vertical plane, the second value being half the first value.

10. The irradiation device of claim 7, further comprising:
    a fastening element that receives the shaft and is attachable to the support; and
    a clamp which clamps the shaft in the fastening element.

11. The irradiation device of claim 7, further comprising a first gear having a first diameter D1 and engaging a second gear having a second diameter D2, the second gear being rotatable about the shaft, wherein $D1=D2(90/\alpha)$, where $\alpha$ is an angle between the support and a vertical axis.

* * * * *